(12) United States Patent
Grison et al.

(10) Patent No.: US 6,228,961 B1
(45) Date of Patent: *May 8, 2001

(54) ALKOXYSILACYCLOALKANES, PROCESS FOR THEIR PREPARATION AND THEIR USE FOR THE POLYMERIZATION OF OLEFINS

(75) Inventors: Claude Grison, Vandoeuvres les Nancy; Valerie Barthel, Guewenheim; Philippe Coutrot, Saulyures les Nancy; Jean-Michel Brusson; Claude Brun, both of Idron; Corinne Meynard, Dax, all of (FR)

(73) Assignee: ELF Atochem S.A., Puteaux (FR)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/715,915

(22) Filed: Sep. 19, 1996

(30) Foreign Application Priority Data

Sep. 20, 1995 (FR) .................................................. 95 11025

(51) Int. Cl.[7] ...................................................... C08F 4/16
(52) U.S. Cl. ...................... 526/194; 556/406; 502/158; 502/125; 502/126; 526/125.3; 526/128; 526/194
(58) Field of Search ................................ 556/406; 502/158, 502/125, 126; 526/125.3, 128, 194

(56) References Cited

U.S. PATENT DOCUMENTS

| 2,464,231 | * | 3/1949 | Hersh | 260/448.2 |
|---|---|---|---|---|
| 3,687,995 | * | 8/1972 | Jonas et al. | 528/10 |
| 3,694,427 |   | 9/1972 | Jonas | 528/12 |
| 4,011,360 | * | 3/1977 | Walsh | 428/402 |
| 4,526,954 | * | 7/1985 | Williams | 518/15 |
| 4,777,278 | * | 10/1988 | Band et al. | 556/480 |
| 4,958,041 |   | 9/1990 | Graefe et al. | 556/480 |
| 5,059,705 | * | 10/1991 | Okinoshima et al. | 556/453 |
| 5,296,624 | * | 3/1994 | Larson et al. | 556/435 |
| 5,498,770 |   | 3/1996 | Hosaka et al. | 502/116 |
| 5,773,537 | * | 6/1998 | Mueller et al. | 526/125.3 |
| 5,868,961 | * | 2/1999 | Shimizu et al. | 252/299.61 |

FOREIGN PATENT DOCUMENTS

| 250 229 | * | 12/1987 | (EP) . |
| 250229 |   | 12/1987 | (EP) . |
| 349693 |   | 3/1990 | (EP) . |
| 665243 |   | 2/1995 | (EP) . |
| 2069504 |   | 3/1971 | (FR) . |

OTHER PUBLICATIONS

Kirk Othmer: Encyclopedia of Chemical Technology, vol. 20, pp. 927–928, 1982.*
Encyclopedia of Polymer Science and Engineering, vol. 15, pp. 226, 228, 1989.*
Kirk Othmer: Encyclopedia of Chemical Technology, vol. 20, pp. 927,928, 1982.*
Chemical Abstracts, vol. 46, No. 6082, 1952 No. 6082i, "Synthesis of Some Organosilicon Compounds by the Grignard Method", M. Kumada.
Chemical Abstracts, vol. 50, No. 8270, 1956, Abst. No. 8270e, "Bond Refractions, Bond Dispersions, and Ring Refractions in Cyclopolymethylenesilanes", B. Smith.

* cited by examiner

Primary Examiner—Margaret G. Moore
(74) Attorney, Agent, or Firm—Smith, Gambrell & Russell, LLP

(57) ABSTRACT

The invention relates to alkoxysilacycloalkanes, to the process for their preparation and to their use in the polymerization of olefins.

The introduction of these alkoxysilacycloalkanes into the olefin polymerization environment makes it possible to raise the heptane-insolubles content of the polymer finally formed.

10 Claims, No Drawings

ALKOXYSILACYCLOALKANES, PROCESS FOR THEIR PREPARATION AND THEIR USE FOR THE POLYMERIZATION OF OLEFINS

FIELD OF THE INVENTION

The invention relates to alkoxysilacycloalkanes, to the process for their preparation and to their use as electron-donor in processes for the polymerization or copolymerization of olefins like propylene or ethylene.

BACKGROUND OF THE INVENTION

A polyolefin which has an excessively high content of heptane-solubles may have a tendency to stick and is therefore difficult to convey and, as a result, is not very suitable for industrial applications. In addition, in the alimentary field, the presence of solubles in a polyolefin which is intended to come into contact with foodstuffs is deemed to be undesirable. For these reasons, for example, isotactic polypropylene preferably has a heptane-insolubles content (denoted by HI, from the expression "heptane-insoluble") higher than 80% by weight.

Patent application EP 250229 teaches that the use of certain silanes during the polymerization of olefins allows the hexane-solubles content of the polyolefin obtained to be reduced.

The paper by R. West, Journal of the American Chemical Society (1954) 76, 6012, describes a method for the preparation of 1,1-dimethoxysilacyclohexane. This preparation involves numerous stages and the intermediate formation of a chlorosilacycloalkane which is particularly tricky to handle and easily degradable.

DESCRIPTION OF THE INVENTION

The process of the present invention is particularly simple, involves raw materials which are easily available and relatively stable and does not involve any chlorosilacycloalkane. The stability of the materials used reduces the risk of side reactions, thereby tending in the direction of better purity of the products which are finally prepared.

The presence of alkoxysilacycloalkanes in the environment for the polymerization or copolymerization of at least one olefin is reflected in an appreciable increase in the polyolefin yield and in an appreciable increase in the HI of the said polyolefin. In addition, the alkoxysilacycloalkane acts as a morphology protector in the suspension and gas-phase polymerization or copolymerization processes. This means that, in the case of these so-called heterogeneous processes, the polymer or copolymer formed is a better morphological replica of the initial solid catalytic component if an alkoxysilacycloalkane is introduced as an external electron-donor into the polymerization or copolymerization environment.

The process according to the invention includes the stage of reaction between an alkylenedimagnesium dibromide of formula Br—Mg—A—Mg—Br in which A is a divalent alkylene radical optionally substituted, for example by an alkyl radical containing, for example, from 1 to 6 carbon atoms, the said alkylene radical containing from 4 to 7 carbon atoms, the optional substituent(s) being excluded, and a tetraalkoxysilane of formula $(OR^1)(OR^2)(OR^3)(OR^4)Si$ in which $R^1$, $R^2$, $R^3$ and $R^4$, which may be identical or different, denote linear or branched, saturated and/or unsaturated hydrocarbon radicals which may include a ring.

The radicals $R^1$, $R^2$, $R^3$ and $R^4$ preferably are alkyl radicals containing from 1 to 6 carbon atoms.

The reaction may be carried out in a solvent which preferably exhibits a Lewis base character, as is the case with ethers. The solvent may, for example, be diethyl ether.

The quantity of inert solvent which is employed may, for example, be such that, assuming the reaction yield to be equal to 100%, the alkoxysilacycloalkane formed is encountered again in a concentration of between 0.05 and 2 moles/liter.

The reaction may be carried out, for example, between 0 and 50° C. for 10 win to 12 hours, if appropriate under pressure if the volatility of the species used makes this necessary, bearing in mind the temperature chosen. Since the reaction is generally exothermic, it is preferable to bring the dibromide and the tetraalkoxysilane into contact gradually and with stirring so as to retain control of the temperature of the mixture. The reaction results in the formation of at least one alkoxysilacycloalkane of formula

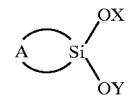

(I)

in which X and Y denote groups forming part of the group of the radicals $R^1$, $R^2$, $R^3$ and $R^4$ and in which A retains the meaning given above. The ring of the alkoxysilacycloalkane therefore contains a silicon atom and a number of carbon atoms equal to the number of carbon atoms which the alkylene radical A contained, the optional substituents of the said alkylene radical being excluded.

The alkoxysilacycloalkanes in the case of which A is an alkylene radical containing at least one alkyl substituent are also a subject-matter of the present invention.

By way of example, Table 1 below mentions some alkoxysilacycloalkanes which can be prepared by the process according to the invention, by reaction of tetramethoxysilane with an alkylenedimagnesium dibromide, depending on the nature of the divalent alkylene radical A included in the alkylenedimagnesium dibromide.

TABLE 1

| Nature of A | Alkoxysilacycloalkane formed |
|---|---|
| tetramethylene | 1,1-dimethoxysilacyclopentane |
| 1-methyltetramethylene | 1,1-dimethoxy-2-methylsilacyclopentane |
| 1-ethyltetramethylene | 1,1-dimethoxy-2-ethylsilacyclopentane |
| 1-n-propyltetramethylene | 1,1-dimethoxy-2-n-propylsilacyclopentane |
| 1-isopropyltetramethylene | 1,1-dimethoxy-2-isopropylsilacyclopentane |
| 1-n-butyltetramethylene | 1,1-dimethoxy-2-n-butylsilacyclopentane |
| pentamethylene | 1,1-dimethoxysilacyclohexane |
| 1-methylpentamethylene | 1,1-dimethoxy-2-methylsilacyclohexane |
| 1-ethylpentamethylene | 1,1-dimethoxy-2-ethylsilacyclohexane |
| 1-n-propylpentamethylene | 1,1-dimethoxy-2-n-propylsilacyclohexane |
| 1-isopropylpentamethylene | 1,1-dimethoxy-2-isopropylsilacyclohexane |
| 1-n-butylpentamethylene | 1,1-dimethoxy-2-n-butylsilacyclohexane |
| 2,3-dimethyltetramethylene | 1,1-dimethoxy-3,4-dimethylsilacyclopentane |
| 1,4-dimethyltetramethylene | 1,1-dimethoxy-2,5-dimethylsilacyclopentane |
| hexamethylene | 1,1-dimethoxysilacycloheptane |

The reaction also gives rise to the formation of BrMgOZ in which Z is a radical forming part of the group of the radicals $R^1$, $R^2$, $R^3$ and $R^4$. This BrMgOZ, considered as being a by-product in the context of the present invention, is generally solid and can, in this case, be removed, for example by filtration. After evaporation of the optional solvent employed and of any excess reactants, the alkoxysilacycloalkane may be purified by distillation, preferably at reduced pressure, for example between 1 and $1\times10^3$ mbar.

The alkylenedimagnesium dibromide of formula Br—Mg—A—Mg—Br may be prepared, for example, by reaction between a dibromoalkane of formula Br—A—Br and magnesium in the presence of a solvent, for example an ether like diethyl ether, for example between 0 and 50° C., if appropriate under pressure if the volatility of the species used demands this, bearing in mind the temperature chosen.

The alkoxysilacycloalkanes capable of being obtained by the process according to the invention may be used as an electron-donor in the polymerization or copolymerization of at least one olefin. For example, the silacycloalkane may be introduced within a solid catalytic component of the Ziegler-Natta type and may act as an internal electron-donor.

It is also possible to employ it as an external electron-donor in an environment for the polymerization or copolymerization of at least one olefin, so as to reduce the hexane-solubles content of the polymer or copolymer finally prepared.

In the case of this latter application (external electron-donor) it is preferred to employ an alkoxysilacycloalkane of formula (I) in which X and Y denote methyl radicals.

The alkoxysilacycloalkane preferably contains at least one alkyl substituent positioned alpha to the silicon atom. Particularly high HI values are obtained when the alkyl substituent contains at least two carbon atoms. An excellent compromise of properties (very high HI and generally high yield) is obtained when the alkyl substituent contains 2 or 3 carbon atoms, as is the case with 1,1-dimethoxy-2-ethylsilacyclopentane, 1,1-dimethoxy-2-n-propylsilacyclopentane, 1,1-dimethoxy-2-isopropylsilacyclopentane, 1,1-dimethoxy-2-ethylsilacyclohexane, 1,1-dimethoxy-2-n-propylsilacyclohexane and 1,1-dimethoxy-2-isopropylsilacyclohexane.

The alkoxysilacycloalkane is generally introduced in a proportion of $1\times10^{-4}$ to 0.2 millimoles per mole of olefin to be polymerized or copolymerized. If the alkoxysilacycloalkane has been prepared in the presence of a solvent of basic character in the Lewis sense, it is recommended to remove the latter before the polymerization or copolymerization stage because it may have an undesirable influence on the structure of the polymers formed. On the other hand, the alkoxysilacycloalkane may be introduced in the presence, for example, of an aliphatic, alicyclic or aromatic hydrocarbon solvent which is not obviously of a basic nature in the Lewis sense, like hexane, cyclohexane or toluene.

A solid catalytic component containing a transition metal is generally introduced into the polymerization or copolymerization environment.

The transition metal may be chosen from the elements of groups 3b, 4b, 5b, 6b, 7b and 8, lanthanides and actinides, of the Periodic Classification of the elements, as defined in the Handbook of Chemistry and Physics, sixty-first edition, 1980–1981. These transition metals are preferably chosen from titanium, vanadium, hafnium, zirconium and chromium.

The solid catalytic component may be of the Ziegler-Natta type and may, for example, be in the form of a complex containing at least the elements Mg, Ti and Cl, the titanium being in the $Ti^{IV}$ and/or $Ti^{III}$ chlorinated form. The solid component may include an electron-donor or acceptor.

A catalytic component of the Ziegler-Natta type is usually the result of the combination of at least one titanium compound, a compound of magnesium and chlorine and optionally an aluminium compound and/or an electron-donor or acceptor, as well as any other compound that can be employed in a component of this type.

The titanium compound is usually chosen from the titanium chlorine compounds of formula $Ti—(OR')_xCl_{4-x}$ in which R' denotes an aliphatic or aromatic hydrocarbon radical containing from one to fourteen carbon atoms or denotes $COR^5$ with $R^5$ denoting an aliphatic or aromatic hydrocarbon radical containing from one to fourteen carbon atoms, and x denotes an integer ranging from 0 to 3.

The magnesium compound is usually chosen from the compounds of formula $Mg(OR^6)_nCl_{2-n}$, in which $R^6$ denotes hydrogen or a linear or cyclic hydrocarbon radical and n denotes an integer ranging from 0 to 2.

The chlorine present in the component of Ziegler-Natta type may originate directly from the titanium halide and/or the magnesium halide. It may also originate from an independent chlorinating agent such as hydrochloric acid or an organic halide like butyl chloride.

Depending on the nature of the transition metal included in the solid catalytic component, it may be necessary to add to the polymerization environment a cocatalyst capable of activating the transition metal of the solid component. If the transition metal is titanium, the cocatalyst may be chosen from organic aluminium derivatives.

This organic aluminium derivative may be a derivative of formula $R^7R^8R^9Al$ in which each of $R^7$, $R^8$ and $R^9$, which may be identical or different, denotes either a hydrogen atom or a halogen atom or an alkyl group containing from 1 to 20 carbon atoms, at least one of $R^7$, $R^8$ and $R^9$ denoting an alkyl group. As an example of suitable compound there may be mentioned ethylaluminium dichloride or dibromide or dihydride, isobutylaluminium dichloride or dibromide or dihydride, diethylaluminium chloride or bromide or hydride, di-n-propylaluminium chloride or bromide or hydride, and diisobutylaluminium chloride or bromide or hydride. A trialkylaluminium such as tri-n-hexylaluminium, triisobutylaluminium, trimethylaluminium and triethylaluminium is employed in preference to the abovementioned compounds.

The cocatalyst may also be an aluminoxane. This aluminoxane may be linear, of formula

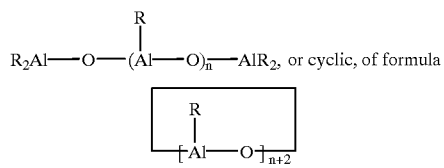

R denoting an alkyl radical containing from one to six carbon atoms and n being an integer ranging from 2 to 40, preferably from 10 to 20. The aluminoxane may include groups R of different nature. All the groups R preferably denote methyl groups. Furthermore, a cocatalyst is also intended to mean mixtures of the abovementioned compounds.

The quantities of cocatalyst which are employed must be sufficient to activate the transition metal. In general, when an organic aluminium derivative is employed as cocatalyst, a quantity thereof is introduced such that the atomic ratio of the aluminium contributed by the cocatalyst to the transition metal(s) which it is desired to activate ranges from 0.5 to 10 000 and preferably from 1 to 1000.

The polymerization or copolymerization process may be conducted in suspension, in solution, in gaseous phase or in bulk.

A bulk polymerization process consists in performing a polymerization in at least one of the olefins to be polymerized which is kept in the liquid or supercritical state.

The solution or suspension polymerization processes consist in performing a polymerization in solution or in suspension in an inert medium and especially in an aliphatic hydrocarbon.

In the case of a solution polymerization process it is possible to employ, for example, a hydrocarbon containing from eight to twelve carbon atoms or a mixture of these hydrocarbons. In the case of a suspension polymerization process it is possible to employ, for example, n-heptane, n-hexane, isohexane, isopentane or isobutane.

The operating conditions for these bulk, solution, suspension or gas-phase polymerization processes are those that are usually proposed for similar cases making use of conventional catalyst systems of the Ziegler-Natta type, whether supported or otherwise.

For example, in the case of a suspension or solution polymerization process it is possible to operate at temperatures ranging up to 250° C. and at pressures ranging from atmospheric pressure to 250 bars. In the case of a polymerization process in liquid propylene medium the temperatures may range up to the critical temperature and the pressures may be included between the atmospheric pressure and the critical pressure. In the case of a bulk polymerization process resulting in polyethylenes or in copolymers in which ethylene predominates it is possible to operate at temperatures of between 130° C. and 350° C. and at pressures ranging from 200 to 3500 bars.

A gas-phase polymerization process may be implemented with the aid of any reactor permitting a gas-phase polymerization and in particular in a reactor containing a stirred bed and/or a fluidized bed.

The conditions for implementing the gas-phase polymerization, especially temperature, pressure, injection of the olefin or of the olefins into the reactor containing a stirred bed and/or a fluidized bed, and control of the polymerization temperature and pressure, are similar to those proposed in the prior art for the gas-phase polymerization of olefins. The operation is generally carried out at a temperature that is lower than the melting point Tm of the polymer prepolymer to be synthesized, and more particularly between +20° C. and (Tm-5)° C., and at a pressure such that the olefin or the olefins are essentially in the vapor phase.

The solution, suspension, bulk or gas-phase polymerization processes may involve a chain transfer agent, so as to control the melt index of the polymer to be produced. The chain transfer agent employed may be hydrogen, which is introduced in a quantity that can range up to 90% and preferably lies between 0.01 and 60 mol % of the combined olefin and hydrogen delivered to the reactor.

The olefins that can be employed for the polymerization or copolymerization are, for example, the olefins containing from two to twenty carbon atoms and in particular the alpha-olefins of this group. Olefins which may be mentioned are ethylene, propylene, 1-butene, 4-methyl-1-pentene, 1-octene, 1-hexene, 3-methyl-1-pentene, 3-methyl-1-butene, 1-decene, 1-tetradecene or mixtures thereof.

The polymerization or copolymerization process according to the invention is particularly suitable for reducing the heptane-solubles content of polymers or copolymers when the polymerization or copolymerization environment includes an olefin containing at least three carbon atoms.

This process is therefore particularly suited for the polymerization or copolymerization of propylene.

EXAMPLES

In the examples which follow the heptane-insolubles content (represented by HI) was measured by extraction of the soluble fraction from the polymer using boiling heptane for two hours in an apparatus of the Kumagawa type.

Examples 1 to 15 a) Preparation of alkylenedimagnesium dibromides

In a 500-ml glass round bottom flask fitted with a water condenser, a thermometer and a mechanical stirring system and which has been purged with argon 0.2 moles of dibromoalkane of formula Br—A—Br in the form of a solution in 200 ml of anhydrous diethyl ether are added to 0.46 moles of magnesium, and this preparation is left stirred for 6 hours at ambient temperature. The preparation is then transferred to a dropping funnel.

b) Preparation of dimethoxysilacycloalkanes.

In a 1.5-liter glass round bottom flask fitted with a mechanical stirring system, a water condenser and a dropping funnel containing the preparation produced in a), and after purging with argon, the preparation produced in a) is added over 2 hours to 0.18 moles of tetramethoxysilane in the form of a solution in 400 ml of diethyl ether at ambient temperature. A heat release takes place and a precipitate appears. When the addition is finished the mixture is stirred for 30 minutes and then heated to reflux for 4 hours. The mixture is then cooled to ambient temperature, the solid being removed by filtration and washed with ether, still under argon atmosphere. The ether is removed in the rotary evaporator at approximately 25° C. at a pressure of 30 mbar. The residue contains a dimethoxysilacycloalkane of formula

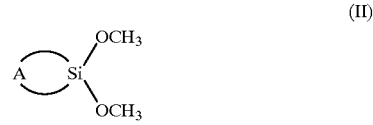

(II)

Table 2 gives the boiling points (b.p.) at a pressure P, of the compounds produced, as a function of the nature of the divalent radicals A employed.

c) Polymerizations in liquid propylene

The following are introduced, in the order shown, into an 8-liter stainless steel reactor fitted with a stirring system and a temperature control, after the reactor has been purged with nitrogen: 2.5 l (STP) of hydrogen, 6 liters of liquid propylene, 30 millimoles of triethylaluminium in the form of a solution in hexane at a concentration of 1.5 moles/liter, and then a dimethoxysilacycloalkane as prepared in b), in the form of a solution in hexane at a concentration of 0.2 moles per liter, so as to conform to an Al/Si molar ratio shown in Table 2. After stirring for 10 minutes at ambient temperature 40 mg of a solid catalytic component prepared as in Example 12 of U.S. Pat. No. 5,212,132 are introduced. With the stirring continued, the temperature of the reactor is next raised to 70° C. over 10 minutes, kept at this temperature for an hour and then the reactor is cooled and decompressed. The results are collected in Table 2.

Example 16

Comparative

Propylene is polymerized in conditions which are equivalent to those described in c) of the preceding examples, except that no alkoxysilacycloalkane is introduced into the polymerization environment. The results are collected in Table 2.

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims. The above references are hereby incorporated by reference.

TABLE 2

| | | PREPARATION OF ALKOXYSILACYCLOALKANES | | | POLYMERIZATIONS | | |
|---|---|---|---|---|---|---|---|
| Example No. | Nature of A | Nature of the dimethoxysilacycloalkane obtained | B.p. (° C.) | P (mbar) | Al/Si | Yield (g/g) | HI (weight %) |
| 1 | tetramethylene | 1,1-dimethoxysilacyclopentane | 63 | 40 | 10 | 8 100 | 61.7 |
| 2 | 1-methyltetramethylene | 1,1-dimethoxy-2-methylsilacyclopentane | 80 | 33 | 10 | 20 640 | 91.3 |
| 3 | 1-ethyltetramethylene | 1,1-dimethoxy-2-ethylsilacyclopentane | 92 | 40 | 10 | 30 240 | 96.2 |
| 4 | 1-n-propyltetramethylene | 1,1-dimethoxy-2-n-propylsilacyclopentane | 104 | 40 | 10 | 24 300 | 95.1 |
| 5 | 1-isopropyltetramethylene | 1,1-dimethoxy-2-isopropylsilacyclopentane | 95–100 | 1.3 | 23 | 36 800 | 94.1 |
| 6 | 1-n-butyltetramethylene | 1,1-dimethoxy-2-n-butylsilacyclopentane | 49–51 | 5.3 | 10 | 27 600 | 94.5 |
| 7 | pentamethylene | 1,1-dimethoxysilacyclohexane | 171 | 1013 | 10 | 10 400 | 82.3 |
| 8 | 1-methylpentamethylene | 1,1-dimethoxy-2-methylsilacyclohexane | 75–78 | 40 | 20 | 35 100 | 96.4 |
| 9 | 1-ethylpentamethylene | 1,1-dimethoxy-2-ethylsilacyclohexane | 102–105 | 40 | 20 | 42 780 | 97.9 |
| 10 | 1-n-propylpentamethylene | 1,1-dimethoxy-2-n-propylsilacyclohexane | 88–90 | 10.7 | 20 | 34 200 | 96.8 |
| 11 | 1-isopropylpentamethylene | 1,1-dimethoxy-2-isopropylsilacyclohexane | 110–115 | 40 | 20 | 29 800 | 96.5 |
| 12 | 1-n-butylpentamethylene | 1,1-dimethoxy-2-n-butylsilacyclohexane | 60–62 | 4 | | | |
| 13 | 2,3-dimethyltetramethylene | 1,1-dimethoxy-3,4-dimethylsilacyclopentane | 68–71 | 40 | 10 | 17 600 | 89.3 |
| 14 | 1,4-dimethyltetramethylene | 1,1-dimethoxy-2,5-dimethylsilacyclopentane | 70 | 40 | 10 | 27 700 | 96 |
| 15 | hexamethylene | 1,1-dimethoxysilacycloheptane | 80 | 40 | | | |
| 16 (comp.) | — | — | | | | 7 400 | 60 |

What is claimed is:

1. A process for the polymerization or copolymerization of at least one olefin, comprising polymerizing or copolymerizing at least one olefin in the presence of an alkoxysilacycloalkane of the formula:

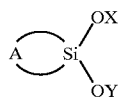

in which X and Y denote hydrocarbon radicals and A denotes a divalent alkylene radical having a backbone of from 4 to 7 carbon atoms, at least one alkyl radical containing 2 to 3 carbon atoms being positioned only alpha to the silicon atom as the only alkyl radical or radicals attached to said backbone, whereby the cyclo portion of said alkoxysilacycloalkane is formed by a silicon atom and the from 4 to 7 carbon atoms of the backbone of the divalent alkylene radical.

2. The process of claim 1, wherein at least one alkyl substituent contains 2 carbon atoms.

3. The process of claim 1, wherein the alkoxysilacycloalkane acts as an external electron-donor, and polymerization or copolymerization of at least one olefin occurs in the presence of a solid catalytic component containing a transition metal and in the presence of an organo aluminum compound.

4. The process of claim 3, wherein at least one olefin contains at least three carbon atoms.

5. The process of claim 4, wherein at least one olefin is propylene.

6. The process of claim 2, wherein the alkoxysilacycloalkane acts as an external electron-donor, and polymerization or copolymerization of at least one olefin occurs in the presence of a solid catalytic component containing a transition metal and in the presence of an organo aluminum compound.

7. The process of claim 6, wherein at least one olefin contains at least three carbon atoms.

8. The process of claim 7, wherein at least one olefin is propylene.

9. A process for the polymerization or copolymerization of at least one olefin, comprising polymerizing or copolymerizing at least one olefin containing at least three carbon atoms in the presence of an alkoxysilacycloalkane of the formula:

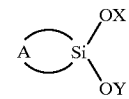

in which X and Y denote hydrocarbon radicals and A denotes a divalent alkylene radical having a backbone of from 4 to 7 carbon atoms, at least one alkyl radical containing 2 to 3 carbon atoms being positioned alpha to the silicon atom;
 whereby the cyclo portion of said alkoxysilacycloalkane is formed by the silicon atom and said backbone, and said alkoxysilacycloalkane acts as an external electron-donor;
 wherein said polymerization or copolymerization occurs in the presence of a solid catalytic component containing a transition metal and in the presence of an organo aluminum compound; and
 wherein the alkoxysilacycloalkane is selected from the group consisting of:
  1,1-dimethoxy-2-ethylsilacyclopentane,
  1,1-dimethoxy-2-n-propylsilacyclopentane,
  1,1-dimethoxy-2-isopropylsilacyclopentane,
  1,1-dimethoxy-2-ethylsilacyclohexane,
  1,1-dimethoxy-2-n-propylsilacyclohexane and
  1,1-dimethoxy-2-isopropylsilacyclohexane.

10. A process for the polymerization or copolymerization of at least one olefin, comprising polymerizing or copolymerizing at least one olefin containing at least three carbon atoms in the presence of an alkoxysilacycloalkane of the formula:

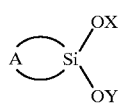

which X and Y denote hydrocarbon radicals and A denotes a divalent alkylene radical having a backbone of from 4 to 7 carbon atoms, at least one alkyl radical containing 2 carbon atoms being positioned alpha to the silicon atom;

whereby the cyclo portion of said alkoxysilacycloalkane is formed by the silicon atom and said backbone, and said alkoxysilacycloalkane acts as an external electron-donor;

wherein said polymerization or copolymerization occurs in the presence of a solid catalytic component containing a transition metal and in the presence of an organo aluminum compound; and wherein said alkoxysilacycloalkane is:
1,1-dimethoxy-2-ethylsilacyclopentane, or
1,1-dimethoxy-2-ethylsilacyclohexane.

* * * * *